United States Patent [19]
Yeng et al.

[11] Patent Number: 5,504,221
[45] Date of Patent: Apr. 2, 1996

[54] METHOD FOR RESOLVING RACEMIC COMPOUNDS

[75] Inventors: Feng-Wen Yeng; Jaw-Yuh Chiu; Chia-Lin J. Wang, all of Taipei, Taiwan

[73] Assignee: Development Center for Biotechnology, Taipei, Taiwan

[21] Appl. No.: 397,846

[22] Filed: Mar. 2, 1995

[51] Int. Cl.$^6$ .................................................. C07D 317/64
[52] U.S. Cl. .................................................. 549/435
[58] Field of Search .......................... 549/435, 436

[56] References Cited

U.S. PATENT DOCUMENTS 4,996,331  2/1991  Kimura et al. .................... 549/229

OTHER PUBLICATIONS

Nelson et al., "A Rapid Total Synthesis of an Ellagitannin", J. Org. Chem. 59:2577–2580, 1994.
Lipshutz et al., "Cyanocuprate–Mediated Intramolecular Biaryl Couplings Applied to an Ellagitannin, Synthesis of (+)–O–Permethyltellimagrandin II", Tetrahedron Letters vol. 35, No. 31, pp. 5567–5570, 1994.

Primary Examiner—Nicky Chan
Attorney, Agent, or Firm—Fish & Richardson

[57] ABSTRACT

A method for resolving racemic dimethyl-4,4'-dimethoxy-5,6,5',6'-di(methylenedioxy)biphenyl-2,2'-dicarboxylate ("DDB"), in which a chiral α-alkyl benzyl alcohol is used as the resolving agent. More specifically, racemic DDB is first hydrolyzed to form dicarboxylic acid, which is then reacted with chiral α-alkyl benzyl alcohol to form two chiral isomers. The chiral isomers, after separation either by chromatography or by recrystalli-zation, are respectively hydrogenated and esterified to form chiral DDB isomers.

23 Claims, No Drawings

METHOD FOR RESOLVING RACEMIC COMPOUNDS

BACKGROUND OF THE INVENTION

The present invention in general relates to a method of resolving racemic dimethyl-4,4'-dimethoxy-5,6,5',6'-di(methylenedioxy)biphenyl-2,2'-dicarboxylate ("DDB") or its analogs.

Antihepatitic drugs include Ara-A, glycyrrhizic acid and the silymaria group. The therapeutic effects of these drugs are not satisfactory. Moreover, some of these medicines are quite expensive. DDB, an intermediate formed in the synthesis of schizandrin C (an ingredient of Fructus schisandrae chinensis), has recently attracted the attention of many researchers in hepatitis therapy. DDB has been clinically proved to possess therapeutic effects in treating hepatitis.

According to the newly promulgated regulations of the U.S. Food and Drug Administration, if a new medicine to be marketed is a racemic isomer mixture, it should be optically resolved into two single phase isomers, and only after the pharmacological, toxicological, safety and clinical reports on the single phase isomers have been submitted can it be put on the market.

Few reports have been directed to the optical resolution of DDB. In *J. Org. Chem.* 1994, 59, 2577–2580, A. I. Meyers, asymmetric synthesis of (S)-hexamethoxydiphenic acid is reported, in which chiral bromo oxazoline is used in the Ullmann coupling reaction. This process has the disadvantages of process complexity and low yield. Bruce H. Lipshutz also discloses the asymmetric synthesis of (s)-hexamethoxydiphenic acid (*Tetrahedron Letters*, 1994, 35, 5567–5570). That process is characterized in combining chiral s,s-stilbene diol with two bromophenyl derivatives, followed by an intramolecular biphenyl coupling reaction. It also has the disadvantage of process complexity. Furthermore, the raw material, chiral s,s-stilbene diol, is expensive. Moreover, the process is not easy to control because many organo-metallic reactions and low temperature reactions are involved.

Zhang Chunzhen discloses a method for resolving DDB in which the resolving reagent used is (−)-strychnine, which is a toxic natural occurring substance (*Kexue Tongbao*, 32 (1), 72, 1987). According to this process, chiral biphenyl dicarboxylic acid is first isolated and then esterified into chiral DDB. The process is also quite complicated.

SUMMARY OF THE INVENTION

It is therefore an object of the invention to provide a simple, low cost, and high-yield method for resolving racemic dimethyl-4,4'-dimethoxy-5,6,5',6'-di(methylenedioxy) biphenyl-2,2'-dicarboxylate.

Chiral α-alkylbenzyl alcohol, the optical resolving reagent used to practice the method of the present invention, displays no toxicity. Furthermore, according to this method, the separation of the intermediates of chiral DDB is rather simple, and can be performed either by chromatography or by recrystallization.

Specifically, the method of the invention includes the steps of (a) hydrolyzing racemic dimethyl-4,4'-dimethoxy-5,6,5',6'-di(methylenedioxy)biphenyl-2,2'-dicarboxylate to obtain 4,4'-dimethoxy-5,6,5',6'-di(methylenedioxy)biphenyl-2,2'-dicarboxylic acid; (b) reacting the 4,4'-dimethoxy-5,6,5',6'-di(methylenedioxy)biphenyl-2,2'-dicarboxylic acid with chiral α-alkylbenzyl alcohol in the presence of N,N'-dicyclohexylcarbodiimide ("DCC") and 4-dimethylaminopyridine ("DMAP") to obtain a mixture of ester products, wherein the mole equivalent ratio of the 4,4'-dimethoxy-5,6,5',6'-di(methylenedioxy)biphenyl-2,2'-dicarboxylic acid to the chiral α-alkylbenzyl alcohol ranges from 1:2 to 1:2.5; (c) separating the mixture into (S) (2R, 2'R) di(α-alkyl)-benzyloxycarbonyl-4,4'-dimethoxy-5,6,5',6'-di(methylenedioxy)biphenyl ("isomer A") and (R) (2R, 2'R) di(α-alkyl)-benzyloxycarbonyl-4,4'-dimethoxy-5,6,5',6'-di(methylenedioxy)biphenyl ("isomer B"); (d) hydrogenating the isomer A or the isomer B to obtain chiral dimethyl-4,4'-dimethoxy-5,6,5',6'-di(methylenedioxy)biphenyl- 2,2'-dicarboxylic acid; and (e) esterifying the chiral dimethyl-4,4'-dimethoxy-5,6,5',6'-di(methylenedioxy)biphenyl-2,2'-dicarboxylic acid.

For the structures of isomers A and B, see the scheme below where R stands for the α-alkyl moiety.

Other features and advantages of the present invention will be apparent from the following description of the preferred embodiments, and also from the claims.

DESCRIPTION OF THE PREFERRED EMBODIMENTS

An illustrative example of the resolution method of this present invention is depicted in the following scheme:

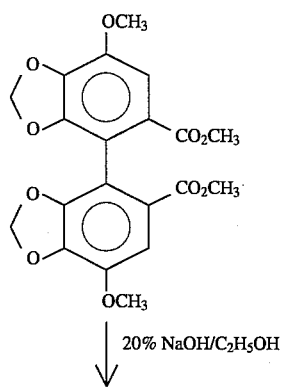

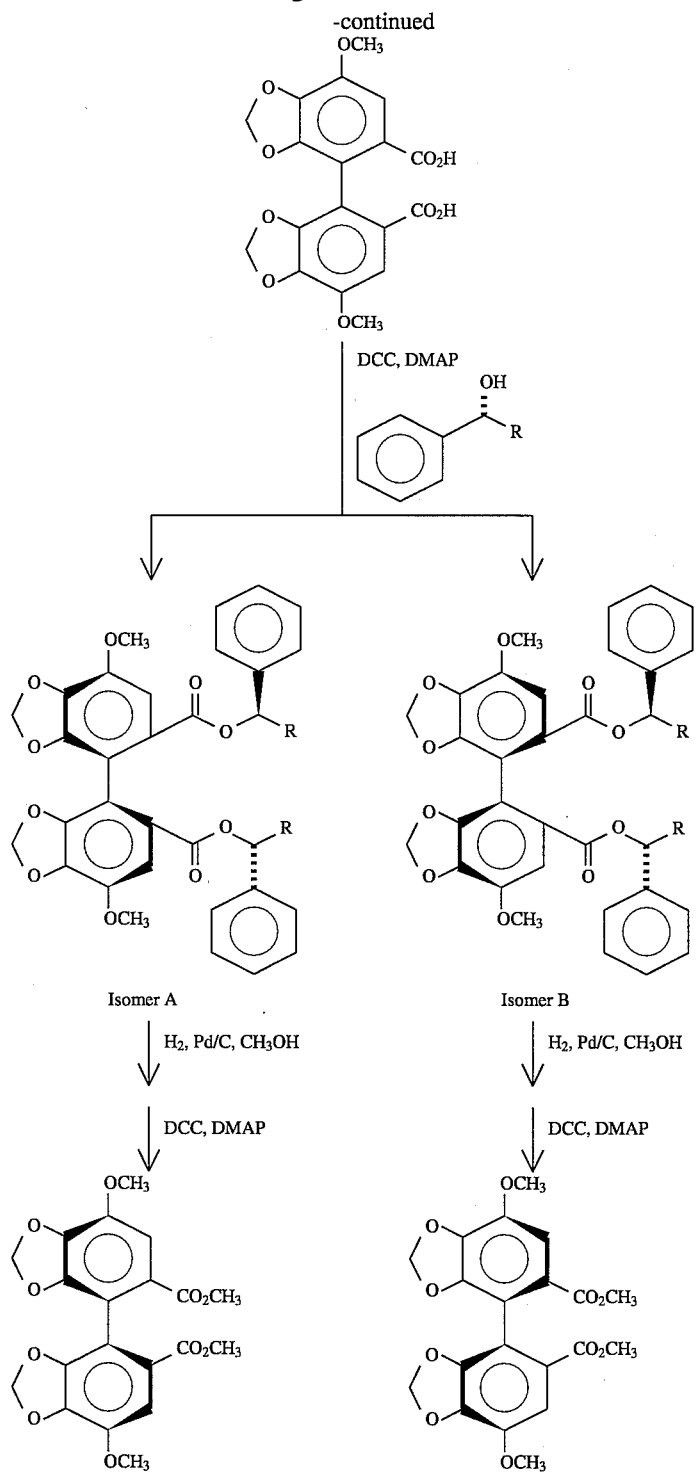

According to the above scheme, racemic DDB is first placed in a mixed solution comprising sodium hydroxide aqueous solution and alcohols. The preferred concentration of the sodium hydroxide is 20–30%. Alcohols suitable for use include, but are not limited to, methanol, ethanol or isopropanol. The mixture of racemic DDB and the mixed solution should be heated to reflux for 12–48 hours. The preferred mixing ratio of racemic DDB, sodium hydroxide aqueous solution, and alcohols is 1 g/10–30 ml/10–30 ml.

The mixture is then cooled to 0° C.–20° C., preferably 0° C., and neutralized to a pH value of 1–6, preferably 3–4 by using 5% hydrochloric acid to obtain white precipitates. After filtration and washing with organic solvents (for example alcohols such as methanol, ethanol or isopropanol, ketones such as acetone, methyl ethyl ketone, and ethers such as ethyl ether, petroleum ether), white solid 4,4'-dimethoxy-5,6,5',6'-di(methylenedioxy)biphenyl-2,2'-dicarboxylic acid is obtained. The yield can be as high as 95–100%.

One mole equivalent of the obtained 4,4'-Dimethoxy-5, 6,5',6'-di(methylenedioxy)biphenyl-2,2'-dicarboxylic acid, 2–3 mole equivalents of N,N'-dicyclohexylcarbodiimide and 0.2–0.3 mole equivalents of 4-dimethylaminopyridine are then dissolved in a solution of dichloromethane or chloroform, and allowed to agitate at room temperature for 1–5 hours, preferably 1–2 hours. Chiral α-alkylbenzyl alcohol is then added to the solution and the resulting solution is agitated for 8–24 hours. Note that the amount of the chiral α-alkylbenzyl alcohol should be in the range of 2–2.5 mole equivalents according to the method of the invention. The α-alkyl group, which contains 1–16 carbon atoms, can be a straight chain, a branched alkyl group, or a cycloalkyl group. A preferred α-alkyl group is a straight chain $C_{6-12}$ group.

The resulting solution is then subjected to filtration, and the filtrate can be washed with 10% hydrochloric acid twice and dried over anhydrous magnesium sulfate. The filtrate thus obtained is thereafter concentrated to obtain a tackified liquid mixture. The tackified liquid mixture is then separated into isomer A and isomer B as indicated in the scheme. The method for separation can be by chromatography or by recrystalli-zation. When using a silica gel packed column, the eluant can be a mixed solvent of ethyl acetate and n-hexane, the mixed ratio thereof is preferably in the range of 1/12 to 1/4 (more preferably, 1/8 to 1/6). Equal amounts of isomer A and isomer B are obtained according to the separation method. The yield of each isomer can be up to 40–45%, and the total yield up to 80–90%. If recrystallization is used, ethyl acetate is first added to the tackified liquid mixture, and heated to a temperature of 40° C.–45° C. until the complete dissolution of the tackified liquid mixture. The amount of the ethyl acetate is preferably 2–3 times the tackified liquid mixture. A solvent, such as n-hexane (e.g., 15–25 times in weight), is then added, and the mixture is heated with agitation for a sufficient period of time (e.g., 10–20 minutes). A large amount of white solid is precipitated after the resulting solution has been cooled (e.g., first cooled to room temperature, and then to 0° C. followed by standing for one day). After filtration, the white solid is then taken out and washed with n-hexane (20–30 times in weight) to give a first crop of white crystalline flakes. The filtrate is concentrated (e.g., to ½ to ⅓ of its original volume) resulting in a repeated precipitation of a white solid. The white solid can be washed with n-hexane to give another crop of white crystalline flakes. Combining the two crops of white crystalline flakes give one isomer, isomer A. Concentrating the secondary filtrate will give another iosmer, iosmer B, which is a lightly yellowish liquid. The yield of each of the two isomers usually ranges from 35 to 40%.

Isomer A or B can then be hydrogenated to form chiral 4,4'-dimethoxy-5,6,5',6'-di(methylenedioxy)biphenyl-2,2'-dicarboxylic acid by adding to it 10–15 times of alcohol solvent and 0.2–0.4 times of palladium/carbon catalysts, and then agitating the mixture under one atmosphere of hydrogen for 1–2 hours. Preferably, the chiral 4,4'-dimethoxy-5, 6,5',6'-dimethylenedioxy-biphenyl-2,2'-dicarboxylic acid obtained is immediately mixed with 2–3 mole equivalents of N,N'-dicyclohexylcarbodiimide and 0.2–0.3 mole equivalents of 4-dimethylaminopyridine, and allowed to be agitated at 0° C. up to room temperature. After filtration, concentration, and recrystallization with dichloromethane, chloroform, or alcohols, a white DDB isomer is obtained. The yield of each DDB isomer can be as high as 90–95%.

Without further elaboration, it is believed that one skilled in the art can, based on the description herein, utilize the present invention to its fullest extent. The following specific example is, therefore, to be construed as merely illustrative, and not limitative of the remainder of the disclosure in any way whatsoever.

Racemic DDB (5 g) was dissolved in a mixed solution of 20% sodium hydroxide (50 ml) and ethanol (50 ml). The resulting solution was then heated to reflux for 24 hours, cooled to room temperature and neutralized with 10% hydrochloric acid to a pH value of 3. A white solid was precipitated. The precipitated white solid, after filtration, was washed with methanol (50 ml) thrice, dried under reduced pressure to give a white solid 4,4'-dimethoxy-5,6, 5',6'-di(methylenedioxy)biphenyl-2,2'-dicarboxylic acid (4.53 g). The yield was 97%.

The obtained white solid (4.53 g, 11.6 mole) was then dissolved in dichloromethane (90 ml), and N,N'-dicyclohexylcarbodiimide (5.0 g, 24.36 mmole) and 4-dimethylaminopyridine (0.26 g, 2.31 mmole) were added, and allowed to agitate for 2 hours. Chiral α-octylbenzyl alcohol (5.11 g, 23.23 mmole) was then immediately added to the solution, and the resulting solution was agitated for 24 hours. The resulting solution was then subjected to filtration, and the dichloromethane filtrate was washed with 10% hydrochloric acid (100 ml) twice, and the organic layer was dried over anhydrous magnesium sulfate. The obtained filtrate was thereafter concentrated to obtain a tackified liquid mixture. The tackified liquid mixture was then chromatographed by using a silica gel packed column, eluted by ethyl acetate/n-hexane (⅛). Isomer A (4.05 g) and isomer B (3.78 g) were obtained. Isomer A was a colorless liquid, Rf value=0.6. The yield of isomer A was 44%. Isomer B was a white solid, Rf value=0.45. The yield of iosmer B was 41%.

The physical data of isomer A are as follows:

Data of spectra $^1H$ NMR 200 MHz (CDCl$_3$), δ value 7.37 (s, 2H), 7.15 (m, 3H), 7.04 (m, 2H), (s, 2H), 5.69 (t, 2H, J=18.5 Hz), 5.55 (s, 2H), 3.93 (s, 6H), 1.61 (m, 4H), 1.13 (m, 24H), 0.86 (t, 6H, J=17 Hz) Mass spectrum, m/z 794

Elemental Analysis Calculated: C %: 72.54; H %: 7.30 Found: C %: 71.23; H %: 7.76 Specific Rotation: $[\alpha]_D^{25}$+ 85.84° (0.93, CHCl$_3$)

The physical data of isomer B are as follows:

Data of spectra $^1H$ NMR 200 MHz (CDCl$_3$), δ value 7.42 (s, 2H), 7.25 (m, 3H), 7.04 (m, 2H), 5.80 (s, 2H), 5.75 (t, 2H, J=18.5 Hz), 5.42 (s, 2H), 3.95 (s, 6H), 1.61 (m, 4H), 1.14 (m, 24H), 0.86 (t, 6H, J=17 Hz) Mass spectrum, m/z 794

Elemental Analysis Calculated: C %: 72.54; H %: 7.30 Found: C %: 72.20; H %: 7.55 Specific Rotation: $[\alpha]_D^{25}$– 11.48° (C 0.23, CHCl$_3$)

Isomer A (4 g, 5 mole) was then dissolved in methanol (40 ml), and palladium/carbon catalyst (800 mg) was added into the solution. The resulting solution was then agitated under one atmosphere of hydrogen for 1 hour. N,N'-dicyclohexylcarbodiimide (2.18 g, 10.6 mmole) and 4-dimethylaminopyridine (0.12 g, 1 mmole) were then immediately added, and allowed to agitate at room temperature for 2 hours. After filtration, concentration of the filtrate, and recrystallization with dichloromethane, chiral DDB isomer (1.95 g) in white powder was obtained. The yield was 93%. The melting point of the product was 168°–169° C.

The physical data of the produced chiral DDB isomer are as follows:

Data of spectra $^1H$ NMR 200 MHz (CDCl$_3$), δ value 7.45 (s, 2H), 6.05 (s, 4H), 4.04 (s, 6H), 3.79 (s, 6H) Mass spectrum, m/z 418

Elemental Analysis Calculated: C %: 57.42; H %: 4.31 Found: C %: 57.32; H %: 4.23 Specific Rotation: $[\alpha]_D^{25}$+ 11.01° (C 0.89, DMF)

Isomer B (3.7 g) was hydrogenated, esterified by the same procedures as indicated above. Another chiral DDB isomer was obtained. The product was a white powder. The melting point was 166°–168° C. The NMR spectra are the same as those of the above chiral DDB isomer. The elemental analysis data and specific rotation are as follows: Calculated: C %: 57.42; H %: 4.31 Found: C %: 57.46; H %: 4.26 Specific Rotation: $[\alpha]_D^{25}$ –11.71 (C 1.01, DMF)

Other Embodiments

From the above description, one skilled in the art can easily ascertain the essential characteristics of the present invention, and without departing from the spirit and scope thereof, can make various changes and modifications of the invention to adapt it to various usages and conditions.

Thus, other embodiments are also within the claims. Indeed, a method of resolving a racemic analog of DDB, (dimethyl-4,4'-diethoxy-5,6,5',6'-di(methylenedioxy)biphenyl-2,2'-dicarboxylate), is also contemplated within the scope of this invention.

What is claimed is:

1. A method for resolving racemic dimethyl-4,4'-dimethoxy-5,6,5',6'-di(methylenedioxy)biphenyl-2,2'-dicarboxylate, comprising the following steps:

hydrolyzing said racemic dimethyl-4,4'-dimethoxy-5,6,5',6'-di(methylenedioxy)biphenyl-2,2'-dicarboxylate to obtain 4,4'-dimethoxy-5,6,5',6'-di(methylenedioxy)biphenyl- 2,2'-dicarboxylic acid;

reacting said 4,4'-dimethoxy-5,6,5',6'-di(methylenedioxy) biphenyl-2,2'-dicarboxylic acid with a chiral α-alkylbenzyl alcohol to obtain a mixture of ester products;

separating said mixture into (S)(2R,2'R)di(α-alkyl)benzyloxycarbonyl-4,4'-dimethoxy-5,6,5',6'-di(methylenedioxy)biphenyl ("isomer A") and (R)(2R,2'R)di(α-alkyl)benzyloxycarbonyl-4,4'-dimethoxy-5,6,5',6'-di(methylenedioxy)biphenyl ("isomer B");

hydrogenating said isomer A or said isomer B to obtain a chiral 4,4'-dimethoxy-5,6,5',6'-di(methylenedioxy)biphenyl- 2,2'-dicarboxylic acid; and esterifying said chiral 4,4'-dimethoxy-5,6,5',6'-di(methylenedioxy)biphenyl- 2,2'-dicarboxylic acid to a dimethyl-4,4'-dimethoxy-5,6,5',6'-di(methylenedioxy)biphenyl- 2,2'-dicarboxylate.

2. The method as claimed in claim 1, wherein said hydrolyzing step is performed by adding racemic dimethyl-4,4'-dimethoxy-5,6,5',6'-di(methylenedioxy) biphenyl-2,2'-dicarboxylate to a mixed solution of sodium hydroxide aqueous solution and alcohol, and heating with reflux for 12 to 48 hours.

3. The method as claimed in claim 1, wherein said reacting step is performed by reacting 1 mole equivalent of 4,4'-dimethoxy-5,6,5',6'-di(methylenedioxy)biphenyl- 2,2'-dicarboxylic acid with 2 mole equivalents of chiral α-alkylbenzyl alcohol.

4. The method as claimed in claim 1, wherein said separating step is performed by eluting said mixture by silica gel chromatography using a mixed solvent of ethyl acetate and n-hexane as eluant.

5. The method as claimed in claim 4, wherein the volume ratio of ethyl acetate to n-hexane of the mixed solvent ranges from 1:12 to 1:4.

6. The method as claimed in claim 1, wherein said separating step is performed by recrystallization using a mixed solvent of ethyl acetate and n-hexane.

7. The method as claimed in claim 6, wherein the volume ratio of ethyl acetate to n-hexane ranges from 1:20 to 1:8.

8. The method as claimed in claim 1, wherein said hydrogenating step is performed by reacting isomer A or isomer B with hydrogen at a hydrogen pressure of 1 atmosphere in the presence of palladium/carbon catalyst.

9. The method as claimed in claim 1, wherein hydrogenating step is performed by adding alcohol into isomer A or isomer B to obtain a solution, and reacting the solution with hydrogen at a hydrogen pressure of 1 atmosphere in the presence of palladium/carbon catalyst.

10. The method as claimed in claim 1, wherein said esterifying step is performed by adding 2–3 mole equivalents of N,N'-dicyclohexylcarbodiimide and 0.2–0.3 mole equivalents of 4-dimethylaminopyridine and agitating at ambient temperature.

11. The method as claimed in claim 1, wherein the alkyl group of said α-alkylbenzyl alcohol is a $C_6$–$C_{12}$ alkyl group.

12. The method as claimed in claim 1, wherein said reacting step is performed in the presence of N,N'-dicyclohexylcarbodiimide and 4-dimethylaminopyridine to obtain a mixture of ester products, wherein the mole equivalent ratio of said 4,4'-dimethoxy-5,6,5',6'-di(methylenedioxy)biphenyl-2,2'-dicarboxylic acid to said chiral α-alkylbenzyl alcohol ranges from 1:2 to 1:2.5.

13. The method as claimed in claim 12, wherein said hydrolyzing step is performed by adding racemic dimethyl-4,4'-dimethoxy-5,6,5',6'-di(methylenedioxy)biphenyl-2,2'-dicarboxylate to a mixed solution of sodium hydroxide aqueous solution and alcohol, and heating with reflux for 12 to 48 hours.

14. The method as claimed in claim 12, wherein said reacting step is performed by reacting 1 mole equivalent of 4,4'-dimethoxy-5,6,5',6'-di(methylenedioxy)biphenyl-2,2'-dicarboxylic acid with 2 mole equivalents of chiral α-alkylbenzyl alcohol.

15. The method as claimed in claim 12, wherein in the reacting step, 2–3 mole equivalents of the N,N'-dicyclohexylcarbodiimide and 0.2–0.3 mole equivalents of 4-dimethylaminopyridine are added to 4,4'-dimethoxy-5,6,5',6'-di(methylenedioxy)biphenyl-2,2'-dicarboxylic acid prior to the reaction.

16. The method as claimed in claim 12, wherein said separating step is performed by eluting said reaction mixture by silica gel chromatography using a mixed solvent of ethyl acetate and n-hexane as eluant.

17. The method as claimed in claim 16, wherein the volume ratio of ethyl acetate to n-hexane of the mixed solvent ranges from 1:12 to 1:4.

18. The method as claimed in claim 12, wherein said separating step is performed by recrystallization using a mixed solvent of ethyl acetate and n-hexane.

19. The method as claimed in claim 18, wherein the volume ratio of ethyl acetate to n-hexane ranges from 1:20 to 1:8.

20. The method as claimed in claim 12, wherein said hydrogenating step is performed by reacting isomer A or isomer B with hydrogen at a hydrogen pressure of 1 atmosphere in the presence of palladium/carbon catalyst.

21. The method as claimed in claim 12, wherein hydrogenating step is performed by adding alcohol into isomer A or isomer B to obtain a solution, reacting the solution with hydrogen at a hydrogen pressure of 1 atmosphere in the presence of palladium/carbon catalyst.

22. The method as claimed in claim 12, wherein said esterifying step is performed by adding 2–3 mole equivalents of N,N'-dicyclohexylcarbodiimide and 0.2–0.3 mole equivalents of 4-dimethylaminopyridine and agitating at ambient temperature.

23. The method as claimed in claim 12, wherein the alkyl group of said α-alkylbenzyl alcohol is a $C_6$–$C_{12}$ alkyl group.

* * * * *